United States Patent [19]

Svenson

[11] Patent Number: 4,746,647
[45] Date of Patent: May 24, 1988

[54] PURIFYING PROTEIN OR PEPTIDE RECOMBINANT DNA PRODUCTS BY ELECTROSEPARATION

[76] Inventor: Stefan Svenson, Brättnevägen 12, S-122 43 Enskede, Sweden

[21] Appl. No.: 834,336

[22] PCT Filed: May 24, 1985

[86] PCT No.: PCT/SE85/00218

§ 371 Date: Mar. 27, 1986

§ 102(e) Date: Mar. 14, 1986

[87] PCT Pub. No.: WO85/05631

PCT Pub. Date: Dec. 19, 1985

[30] Foreign Application Priority Data

May 28, 1984 [SE] Sweden ................................ 8402861

[51] Int. Cl.$^4$ ........................ C07K 1/14; C07K 3/12; C07K 3/14; C12N 15/00
[52] U.S. Cl. ..................... 514/3; 204/182.6; 424/85; 424/88; 424/92; 424/1.1; 514/2; 514/21; 530/300; 530/303; 530/350; 530/371; 530/413; 530/417
[58] Field of Search ............... 530/303, 350, 371, 413, 530/417, 300; 204/182.6; 424/1.1, 88, 92, 85; 514/2, 3, 21

[56] References Cited

U.S. PATENT DOCUMENTS

| 3,600,378 | 8/1971 | Marsh et al. ................... 424/92 X |
| 4,185,090 | 1/1980 | McIntire ........................... 424/88 X |
| 4,228,068 | 10/1980 | Wilhelm ........................ 530/825 X |
| 4,276,140 | 6/1981 | Jain ................................... 424/85 X |
| 4,321,192 | 3/1982 | Jain ................................. 424/101 X |
| 4,322,275 | 3/1982 | Jain ................................. 424/101 X |
| 4,351,710 | 9/1982 | Jain ..................................... 424/101 |
| 4,426,323 | 1/1984 | Jain ................................... 424/85 X |
| 4,578,269 | 3/1986 | Morrin ............................ 530/350 X |
| 4,612,283 | 9/1986 | Sugahara et al. ................ 424/88 X |
| 4,694,074 | 9/1987 | Uemura et al. .................... 530/417 |

OTHER PUBLICATIONS

Medline Report No. 1,830,633/79, 205,633.
Medline Report No. 0,693,843/82, 138,843.
Pharm. Ind., vol. 38, pp. 827-831, published 1976 (Koppensteiner, G. et al.) "Versuche zur Entypyrogenisierung parenteralen Arzneimittel".
Biochemistry, vol. 22, pp. 2007-2013, published 1983 (Coughlin, R. T. et al.) "Physical Properties of Define Lipopolysaccharide Salt".
European J. Biochem, vol. 122, pp. 233-237, published 1982 (Brade, H. and Galanos, C.) "Isolation, Purification and Chemical Analysis of the Lipopolysaccharide and Lipid A of Acinetobacter Calcoaceticus NCTC 10305".

*Primary Examiner*—Howard E. Schain
*Attorney, Agent, or Firm*—Bacon & Thomas

[57] ABSTRACT

A method of purifying a contaminated product (protein/peptide) produced by rDNA technique, from hydrophobic contaminants which are charged and originate from the microbial cloning host employed, and the product thus purified are disclosed. The contaminated product is subjected to electroseparation, such as electrodialysis, to remove the contaminants. A charge-providing pretreatment is resorted to when the contaminants themselves are not charged enough to enable them to be directly separated upon electroseparation. In addition, a method of checking the purity of a product (protein/peptide) produced by rDNA technique is disclosed. Moreover, a method of checking the efficiency of the purification process used for purifying a product is disclosed.

6 Claims, 3 Drawing Sheets

PURIFYING PROTEIN OR PEPTIDE RECOMBINANT DNA PRODUCTS BY ELECTROSEPARATION

The present invention concerns the purification of biological material, more particularly the purification of contaminated products (peptides/proteins) which have been produced using recombinant DNA (rDNA) technique.

In the preparation of products (proteins/peptides) by rDNA technique, use is made of microbial cloning hosts, primarily bacteria or yeast.

During the working-up and purification of these rDNA-produced products, one has mainly used permeation gel chromatography utilising e.g. Sephadex ®, ion exchange chromatography and/or HPLC with different types of columns, including reverse phase columns. All of these purification methods have aimed at the removal of microbial contaminants originating from the cloning hosts (so-called E. coli peptides, EPC) (cf. "Journalen", Vol. 3, No. 12, 1983, pp. 331-334, published by Kabi-Vitrum Sverige AB). These methods have up to now been considered efficient enough to remove the above-mentioned contaminating host contaminants. Checking the purity of such products has most often been performed by different types of polyacrylamide gel electrophoresis techniques including the use of dissociating agents such as SDS etc. Also, different types of immuno-assays, such as ELISA and RIA, have been used. Moreover, one has frequently performed pyrogenicity tests and Limulus amoebocyte lysate (LAL) tests.

In spite of the above-mentioned purification methods, the products produced by rDNA technique have still been shown to elicit antibodies directed against these products (proteins/peptides), even though this formation of antibodies has been deemed to be small and, perhaps, medically acceptable. Nevertheless, experts within this field have put forward that caution should be exercised in the registration of these products. ("Lä kartidningen", Vol. 81, No. 8, 1984, p. 636 "Proceed slowly in registering biosynthetic drugs!"). However, in those instances where the protein is to be administered over long periods of time, such as in life-long diseases (e.g. diabetes), not even a slight antibody formation is acceptable.

The basis of the present invention is the insight that also contaminants other than proteins/peptides from the microbial cloning host may give rise to immune reactions.

The invention is based upon research results which show that, due to hydrophobic interaction, minor amounts of hydrophobic contaminants from the microbial cloning host may stick to the product (peptide/protein) during the working-up thereof from the rDNA production environment employed. These hydrophobic contaminants which firmly attach to the product will then constitute epitopes and create fusion epitopes which will elicit antibody formation, not only against the contaminant in question, but also against the product produced by rDNA technique.

The purification methods previously employed have been too "mild" to free the product produced by rDNA technique from these hydrophobic contaminants, and the contaminants which most often are smaller than the product (the peptide/protein) have therefore been carried along during the working-up and purification without being detected.

In the method according to the present invention, these hydrophobic contaminants which result in the formation of epitopes and fusion epitopes, are removed by electroseparation, such as electroseparation using gel-forming substances or electrodialysis, whereby the hydrophobic contaminants are separated from the product (the peptide/protein) such that the purified product will not give rise to immune reactions upon administration to mammals, including man.

The invention relates to a method of purifying a contaminated product (protein/peptide) which has been produced by rDNA technique in that the contaminated product is purified from hydrophobic contaminants which are charged and which originate from the microbial cloning host employed, such that the product is subjected to electroseparation to remove the contaminants. In addition, the invention comprises that the hydrophobic contaminants may obtain at least part of their charge by a charge-providing pretreatment, such as mild alkaline treatment, dissociation by means of dissociating agents, treatment with kaotropic ions or chelate-forming substances. The preferred electroseparation is electrodialysis. According to one embodiment of the invention, the contaminated product is insulin produced by rDNA technique, and the hydrophobic contaminants are lipopolysaccharides originating from *Escherichia coli*.

The invention also comprises a method of checking the purity of a product (protein/peptide) produced by rDNA technique, in that the product is combined with antibodies directed against hydrophobic contaminants from the microbial cloning host utilised in the production, whereupon a possible binding of the antibodies to the product is detected.

A method of checking the efficiency of the purification process used for purifying a product (protein/peptide) produced by rDNA technique involves combining the product, prior to purification, with a predetermined amount of radioactively or otherwise labelled hydrophobic host contaminant, whereupon the product is subjected to the purification process and the amount of labelled contaminant in the purified product is determined.

Furthermore, the invention comprises the purified product (protein/peptide) which has been obtained after the product has been purified by the purification method according to the invention.

The hydrophobic contaminants from the microbial cloning host employed are frequently inherently charged enough and may therefore be directly separated from the contaminated product when this is subjected to electroseparation, such as electrodialysis. In those instances where the hydrophobic contaminants are not sufficiently charged themselves to make them directly separable upon electroseparation, different charge-providing pretreatments may be resorted to, such as mild alkaline treatment, dissociation by means of dissociating agents, such as urea or guanidine hydrochloride, the use of kaotropic ions, such as potassium ions, or use of chelate-forming substances, such as EDTA.

There are two different methods of checking whether the product (protein/peptide) produced by rDNA technique is free from contaminating hydrophobic host contaminant. According to the first method, the product is combined with antibodies directed against hydrophobic contaminants from the microbial cloning host utilised in the production. If the antibodies bind to the product, the product is contaminated by host contaminants. Detecting the amount of antibodies that have been bound to the product is carried out by, for example, the ELISA test and is a measure of the degree to which the product has been purified. As a result, the efficiency of different purification methods regarding the removal of contaminating host contaminants may be determined.

The other method of checking the purity of the product that has been produced by rDNA technique and/or when the product has been isolated from another source, involves combining the product, prior to purification, with a predetermined amount of radioactively or otherwise labelled hydrophobic host contaminant, whereupon the product contaminated by labelled host contaminant and, possibly, unlabelled host contaminant is purified, whereupon the amount of labelled host contaminant in the purified product is determined. If no labelled host contaminant is detected in the product, the product is pure. If a labelled host contaminant is detected in the purified product, purification has not been efficient enough to remove all host contaminants, i.e. if the product is contaminated by labelled contaminant, it is also contaminated by unlabelled contaminant. This makes it possible to determine the efficiency of different purification methods.

The microbial cloning host which at present is most frequently employed is *Escherichia coli* K 12, but also other bacterial hosts, besides *E. coli*, are used for this purpose, for example *Bacillus subtilis* and *Staphylococcus aureus*. Experiments with yeast, such as *Saccharomyces cerevisiae*, have also been reported.

rDNA technique is already being used in the production of many potential drugs, such as human growth hormone, insulin and interferon, but so far the only protein available on the Swedish market and produced by rDNA technique is insulin bearing the trade mark Humulin ®. Humulin ® has been produced using *E. coli* K 12 as cloning host. In the above-mentioned article in "Journalen", Vol. 3, No. 12, 1983, published by Kabi-Vitrum Sverige AB, it is reported on p. 333 that it is possible, although with some difficulty, to obtain antibodies by means of complete Freund's adjuvant and to sensitise experimental animals against *E. coli* polypeptides (ECP) (originating from the host employed in the production of Humulin ®, but without the genetic code for the A and B chains in insulin). In addition, it appears that Humulin ® is not pyrogenic in rabbits and contained <0.6 ng/mg of bacterial so-called endotoxin, which is equal to lipopolysaccharide (LPS). Neither could endotoxin (LPS) be shown in the Limulus amoebocyte lysate (LAL) test which by many is regarded as the most sensitive test for endotoxin (LPS). The relevance of the LAL test has, however, been questioned, in particular when LPS is present in combination with other hydrophobic substances.

From what has been stated above, one might conclude that it has not been possible with prior art technique to establish in vitro small amounts of microbial contaminants. In accordance with what has been said above, these products may nevertheless give rise to antibody formation, not only against the contaminants mentioned, but also against the product. Of particular interest in this context is that endotoxin (LPS) is a very potent immunological substance. LPS is, in fact, one of the most potent polyclonal B cell stimulating substances that are known.

The experiments described below show that small amounts of endotoxin from the cloning host *E. coli* which consists of lipopolysaccharides, will stick to Humulin ® as is shown by means of radioactively labelled lipopolysaccharide from *E. coli* K 12.

Moreover, it is shown that this radioactively labelled contaminant accompanies Humulin ® upon gel chromatography. By means of the experimentally contaminated Humulin ® it is shown that the radioactively labelled lipopolysaccharide from *E. coli* K 12 (i.e. the host) detaches itself aand is removed from the Humulin ® upon purification by electrodialysis.

MATERIALS UTILISED IN THE EXAMPLES

Humulin ® regular for inject. sc. 40 IU/ml, (Kabi-Vitrum, Sweden). U-$^{14}$C-labelled *E. coli* K 12 LPS (1000 cpm/µg), labelled in vivo with U-$^{14}$C-galactose and U-$^{14}$C-glucose (NEC-520 and NEC-042, NEN, Great Britain) which has been purified by so-called PCP extraction and whose purity has been verified by SDS polyacrylamide gel electrophoresis with subsequent silver colouring and autoradiography. A study with $^1$H-NMR which involved comparison with non-radioactively labelled reference LPS from *E. coli* K 12, showed that this LPS was pure.

For the permeation gel chromatography experiments use was made of Sepharose ® G 75 (Pharmacia, Uppsala, Sweden), the eluent consisting of double-glass distilled water containing 16 mg/lm of glycerol p.a. (Merck, Federal Republic of Germany).

Figure 3:
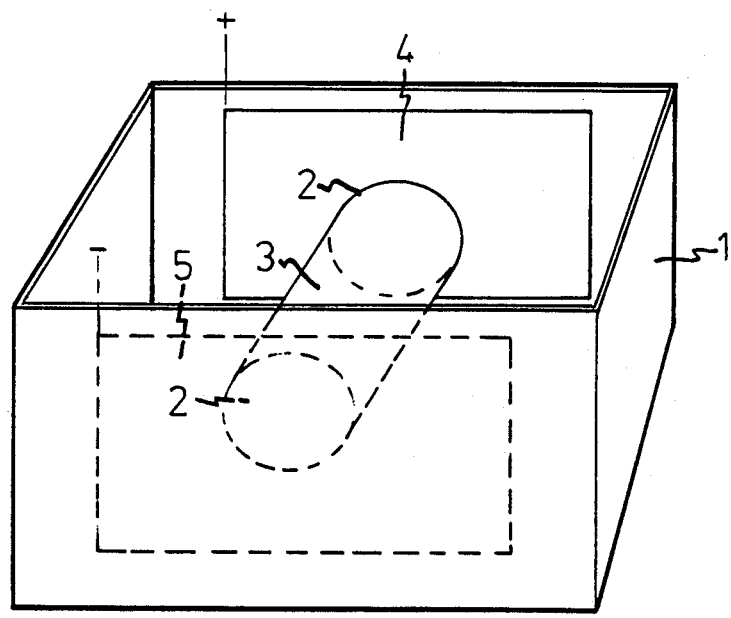
FIG. 3 illustrates schematically an open dialysis-electrodialysis vessel 1 (which is used in Example 2) of, for example, plexiglass and a tubular dialysis chamber 3 closed by means of two dialysis membranes 2. 4 and 5 denote, respectively, a platinum anode and a platinum cathode.

In the electrodialysis experiment, use was made of an electrodialysis bath (see FIG. 3 (1)) and a power unit (LKB, type 2197 Power Supply, LKB, Sweden) using 160 V and 20 mA. The electrodialysis conditions included using the above-mentioned water-glycerol system and dialysis membranes (Union Carbide dialysis membrane 21 DM00C227 P7F20, Union Carbide, Chicago, USA).

EXAMPLE 1

Studying the binding of $^{14}$C-labelled *E. coli* K 12 LPS to Humulin ®

Figure 1:
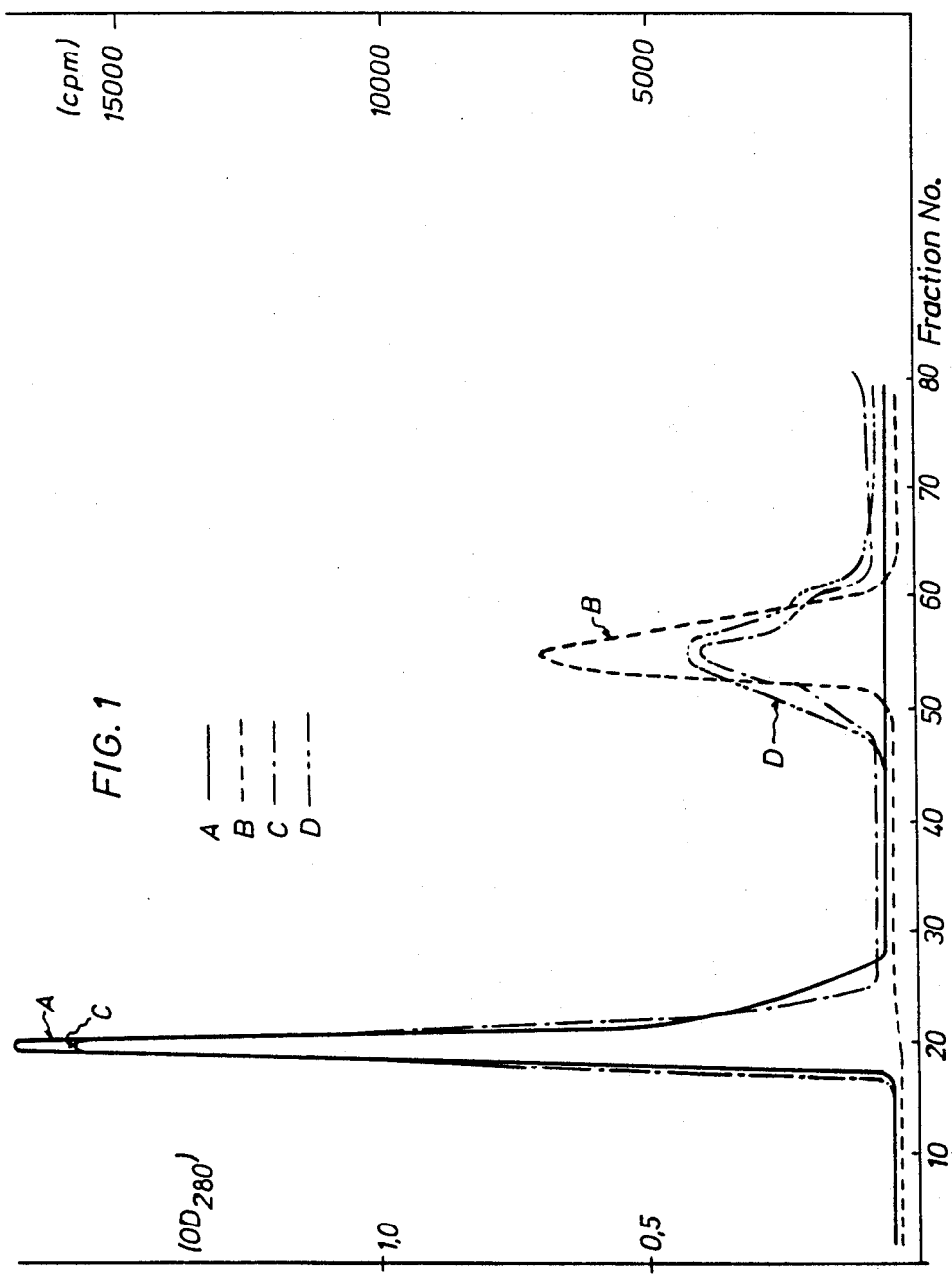
FIG. 1 illustrates gel chromatography of $^{14}$C-labelled *E. coli* K 12 LPS (curve A), Humulin ® [in $OD_{280}$] (curve B), $^{14}$C-labelled *E. coli* K 12 LPS+Humulin ® /in cpm/(curve C), and $^{14}$C-labelled *E. coli* K 12 LPS+Humulin ®/in $OD_{280}$/(curve D). The experimental conditions employed were: column Sepharose ® G 75 (9 mm×550 nm) eluted with $H_2O$-16 mg/ml; flow 4.0 ml/h; fraction volume 0.5 ml.

2.5 mg Humulin ® (as determined by Bio-Rad protein analysis, Bio-Rad, Munich, Federal Republic of Germany) in 1.0 ml water/glycerol according to the above, were mixed with 100 μg of $^{14}$C-labelled *E. coli* K 12 LPS and incubated at room temperature (23° C.) under slight agitation for 2 hours. After that, this mixture was applied to the G75 column (described above). The elution profile of this mixture is shown in FIG. 1 (see curves C and D). This experiment clearly shows that a major proportion of the $^{14}$C-labelled LPS comigrated with Humulin ®. Furthermore, FIG. 1 shows that Humulin ® alone has a retention time which is largely identical with the retention time of the experimentally contaminated Humulin ® (see FIG. 1, curve B). In addition, FIG. 1 shows (curve A) that when only $^{14}$C-labelled LPS was applied, it was eluted out with the initial fraction (void) and that it therefore has a retention time which is completely and distinctly different from that of the mixed product. The reason why this last-mentioned elution profile with only $^{14}$C-labelled LPS is obtained is that this LPS is present in the form of micells.

To sum up, it may be said that $^{14}$C-labelled *E. coli* K 12 LPS binds strongly to Humulin ®.

EXAMPLE 2

Figure 2:
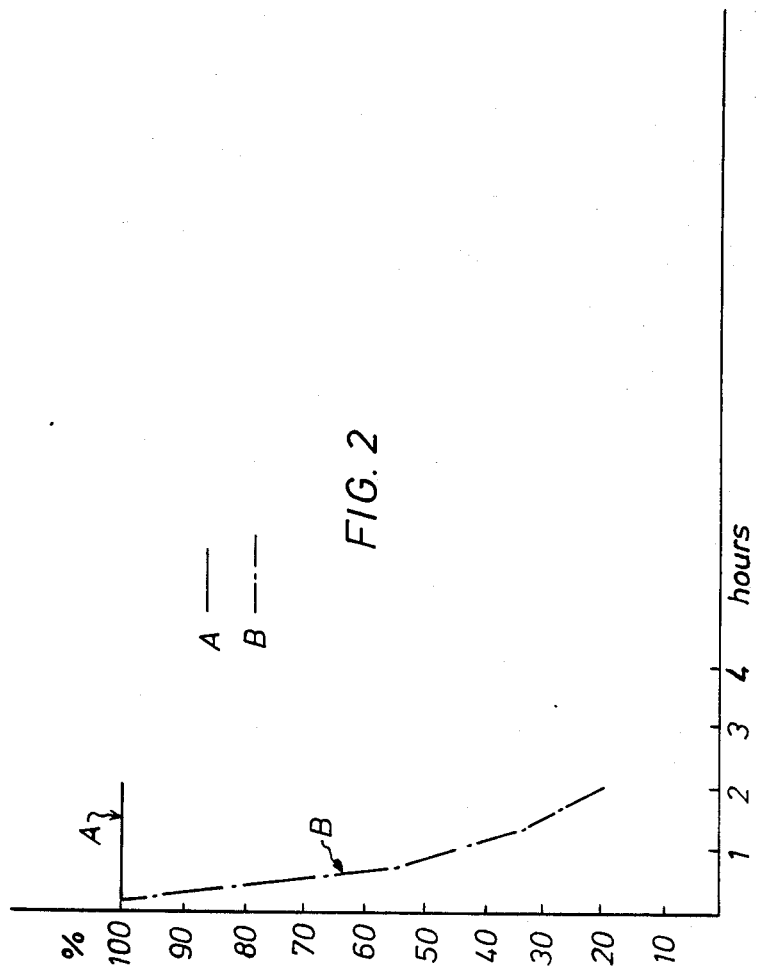
FIG. 2 illustrates electrodialysis purification of Humulin ® from contaminating *E. coli* K 12 LPS, curve A indicating the percentage of remaining Humulin ®, and curve B indicating the percentage of remaining $^{14}$C-labelled radioactive *E. coli* K 12 LPS.

Studying purification of experimentally contaminated Humulin ® by electrodialysis The Humulin ® in fractions 48–63 "purified" by gel permeation chromatography on G75 in accordance with Example 1 was combined, and the total radioactivity was determined to 6,000 cpm (counts per minute) in a total of 7.53 ml. This radioactivity in Humulin ® thus corresponds to an amount of LPS of 6 μg distributed on 2.5 mg Humulin ®, i.e. each milligram of Humulin ® carries 2.4 μg contaminating *E. coli* K 12 LPS. The present Example indicates the removal of this contaminant by electroseparation, use being made of the above-mentioned material and the apparatus schematically illustrated in FIG. 3. This contaminated Humulin ® fraction was subjected to electrodialysis (160 V, 20 mA), and samples were taken at different times. The amount of radioactivity in the dialysis membranes and the amount of Humulin ® were determined. FIG. 2 shows the result, and it appears that during the entire time of the experiment all Humulin ® remained within the dialysis membranes (see curve A), but that the $^{14}$C-labelled *E. coli* LPS had decreased to 55% already after an electrodialysis time of 40 min (see curve B). After 2 hours of electrodialysis, only 17% of the contaminating LPS remained.

To sum up, it may be said that electroseparation according to this experiment by electrodialysis shows that contaminating hydrophobic substances from the host (LPS) may be efficiently removed from rDNA-produced products (proteins/peptides).

EXAMPLE 3

Checking the purity of a product by mixing the product with antibodies directed against hydrophobic contaminants.

Monoclonal antibodies of IgG and IgM classes were produced in Balb/c mice by hybridisation of lymphocytes isolated from the spleen of mice immunised with purified lipopolysaccharide (LPS) from *E. coli* K 12 with sp2 cells to yield hybridoma clones which by enzyme-linked immunosorbent-assay (ELISA) were screened for specific expression of Ig with specificity for the coreoligosaccharide portion of said LPS using that LPS as coating antigen in the ELISA tests. After subsequent subcloning to yield monoclonal antibody producing hybridomas by dilution technique, these hybridomas were propagated both in vitro and in vivo (i.e. as ascites in Balb/c mice). The monoclonal antibodies were isolated using either conventional gel permeation chromatography (IgM) or by using the protein A-affinity chromatography method for isolating IgG monoclonal antibodies.

The purity of each of the used monoclonal antibody preparations was assured by isoelectric focusing pattern, subclass and light chain identification using commercially available light and heavy chain specific anti-mouse antibodies in double radial immune diffusion tests.

Purified pig insulin from Novo, Novo Industri A/S, Novo Alle, 2880 Bagsvaerd, Denmark, was experimentally contaminated with $^{14}$-labelled purified *E. coli* LPS by mixing Actrapid 400 IU with 0.1 mg of LPS in a total volume of 10 ml. After incubation at 25° C. for 5 hours the mixture was chromatographed on Sepharose ® G75 (Pharmacia, Sweden) and the insulin as judged by measurements of the optical density at 280 nanometers was collected.

This preparation was after extensive dialysis against distilled water, containing 1% glycerol and 0.7M NaCl, used as coating antigen in ELISA and compared to the non-contaminated original product for specific binding of mouse-anti *E. coli* K 12 coreoligosaccharide specific monoclonal IgG antibodies prepared as described above. The coating doses of each of the two antigens were logarithmic dilutions from 1000 micrograms protein (as measured by Lowry et al) to 0.001 micrograms per ml.

In the ELISA tests the experimentally contaminated product showed binding of the mouse monoclonal anti-*E. coli* coreoligosaccharide IgG antibodies down to a level of contamination of less than 0.01 microgram of *E. coli* K 12 LPS per mg of insulin.

This Example shows that monoclonal antibodies directed against hydrophobic host contaminants (LPS) accompanying the product protein bind to the product protein if this is contaminated.

I claim:

1. A method of purifying a protein/peptide product produced by rDNA techniques using a microbial cloning host, to remove charged hydrophobic contaminants which originate from the microbial cloning host and which form epitopes and fusion epitopes with the product, which comprises subjecting the product containing the epitopes and fusion epitopes to electroseparation under conditions which separate the hydrophobic contaminant from the product to yield a purified product which will not give rise to immune reactions upon administration to mammals, including man.

2. A method as claimed in claim 1, wherein the hydrophobic contaminants are given at least a part of their charge by a charge providing pretreatment.

3. A method as claimed in claim 2, wherein the pretreatment comprises a mild alkaline treatment, dissociation by means of dissociating agent, treatment with kaotropic ions, or with chelate-forming substances.

4. A method as claimed in claim 1, wherein the electroseparation is conducted by electrodialysis.

5. A method as claimed in claim 1, wherein the contaminated product is insulin.

6. A method as claimed in claim 1, wherein the hydrophobic contaminants consist of lipopolysaccharides originating from *Escherichia coli*.

* * * * *